(12) United States Patent
Baroni et al.

(10) Patent No.: US 7,186,720 B2
(45) Date of Patent: Mar. 6, 2007

(54) TETRAHYDROPYRIDYL-ALKYL-HETEROCYCLES, METHOD FOR PREPARING THE SAME AND PHARMACEUTICAL COMPOSITIONS CONTAINING THE SAME

(75) Inventors: Marco Baroni, Vanzago-Milano (IT); Bernard Bourrie, Saint-Gely-du-Fesc (FR); Pierre Casellas, Montpellier (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 10/475,460

(22) PCT Filed: Apr. 19, 2002

(86) PCT No.: PCT/FR02/01343

§ 371 (c)(1),
(2), (4) Date: Oct. 20, 2003

(87) PCT Pub. No.: WO02/085888

PCT Pub. Date: Oct. 31, 2002

(65) Prior Publication Data
US 2004/0138264 A1 Jul. 15, 2004

(30) Foreign Application Priority Data
Apr. 20, 2001 (FR) .................................. 01 05360
Apr. 20, 2001 (FR) .................................. 01 05362

(51) Int. Cl.
*A61K 31/498* (2006.01)
*A61K 31/502* (2006.01)
*A61K 31/4709* (2006.01)
*A61K 31/4439* (2006.01)
*C07D 401/06* (2006.01)
*C07D 401/14* (2006.01)

(52) U.S. Cl. .................. 514/248; 514/249; 514/266.21; 514/307; 514/314; 514/338; 514/339; 544/235; 544/237; 544/284; 544/353; 546/148; 546/166; 546/256; 546/273.4; 546/275.7; 546/277.4

(58) Field of Classification Search ................ 546/256, 546/277.4, 278.1, 148, 166, 273.4, 275.7; 514/333, 339, 249, 266.21, 307, 314, 338; 544/235, 237, 284, 353
See application file for complete search history.

(56) References Cited

U.S. PATENT DOCUMENTS

| 5,981,754 A | 11/1999 | Badone et al. |
| 6,344,464 B1 | 2/2002 | Bourrie et al. |

FOREIGN PATENT DOCUMENTS

| EP | 0 164 633 | 12/1985 |
| WO | WO 97/01536 | 1/1997 |
| WO | WO 98/48802 | 11/1998 |

OTHER PUBLICATIONS

Bourrie, Bernard et al., "The neuroprotective agent SR57746A abrogates experimental autoimmune encephalomyelitis and impairs associated blood-brain barrier disruption: implications for multiple sclerosis treatment"; Proc. Natl. Acad. Sci. U.S.A.; 1999; 96(22). 12855-12859.

*Primary Examiner*—Bernard Dentz
(74) *Attorney, Agent, or Firm*—Paul E. Dupont; Julie Anne Knight; Robert J. Kajubi

(57) ABSTRACT

The present invention relates to compounds of formula (I):

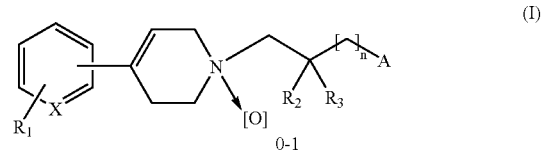

in which X represents N or CH; $R_1$ represents a hydrogen or halogen atom or a $CF_3$ group; $R_2$ and $R_3$ independently represent a hydrogen atom or a methyl group; n is 0 or 1; A represents an optionally substituted nitrogenous heterocycle; and to their N-oxides and to their salts or solvates, to the pharmaceutical compositions and the medicaments comprising them, and to a process for their preparation.

20 Claims, No Drawings

TETRAHYDROPYRIDYL-ALKYL-HETEROCYCLES, METHOD FOR PREPARING THE SAME AND PHARMACEUTICAL COMPOSITIONS CONTAINING THE SAME

CROSS REFERENCE TO RELATED APPLICATIONS

This application is a national stage entry filed under 35 U.S.C. §371, and claims the benefit of priority of International Application No. of PCT/FR02/01343 filed Apr. 19, 2002, which claims priority to French Patent Application Nos. 01 05360 and 01 05362 filed on Apr. 4, 2001.

FIELD OF THE INVENTION

The present invention relates to novel (tetrahydropyridyl)(alkyl)heterocycles, to the pharmaceutical compositions comprising them and to a process for their preparation.

BACKGROUND OF THE INVENTION

U.S. Pat. No. 5,118,691 and U.S. Pat. No. 5,620,988 disclose tetrahydropyridines substituted by a quinolyl-3-alkyl radical which show a dopaminergic activity.

Dukic S. et al. (Arch. Pharm., 1997, 330 (1/2), 25–28) disclose phenylpiperidines carrying a benzimidazol-5-yl-ethyl substituent which also show a dopaminergic activity.

EP 164 633 discloses tetrahydropyridines substituted by a 4-indolyl radical which show an activity with regard to the central nervous system.

It has now been found that some phenyl- and pyridyltetrahydropyridines substituted by nitrogenous heterocycles have a powerful activity with regard to modulating TNF-α (Tumour Necrosis Factor).

TNF-α is a cytokine which has recently aroused interest as mediator of immunity, inflammation, cell proliferation, fibrosis, and the like. This mediator is extensively present in inflamed synovial tissue and exerts an important role in the pathogenesis of autoimmunity (Annu. Rep. Med. Chem., 1997, 32, 241–250).

SUMMARY OF THE INVENTION

Thus, the present invention relates, according to one of its aspects, to (tetrahydro-pyridyl)(alkyl)heterocycles of formula (I):

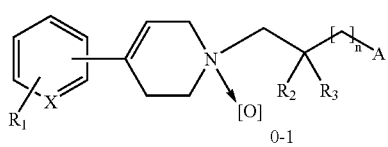

in which
X represents N or CH;
$R_1$ represents a hydrogen or halogen atom or a $CF_3$ group;
$R_2$ and $R_3$ independently represent a hydrogen atom or a methyl group;
n is 0 or 1;
A represents a nitrogenous heterocycle of formula (a)–(i) and (l)

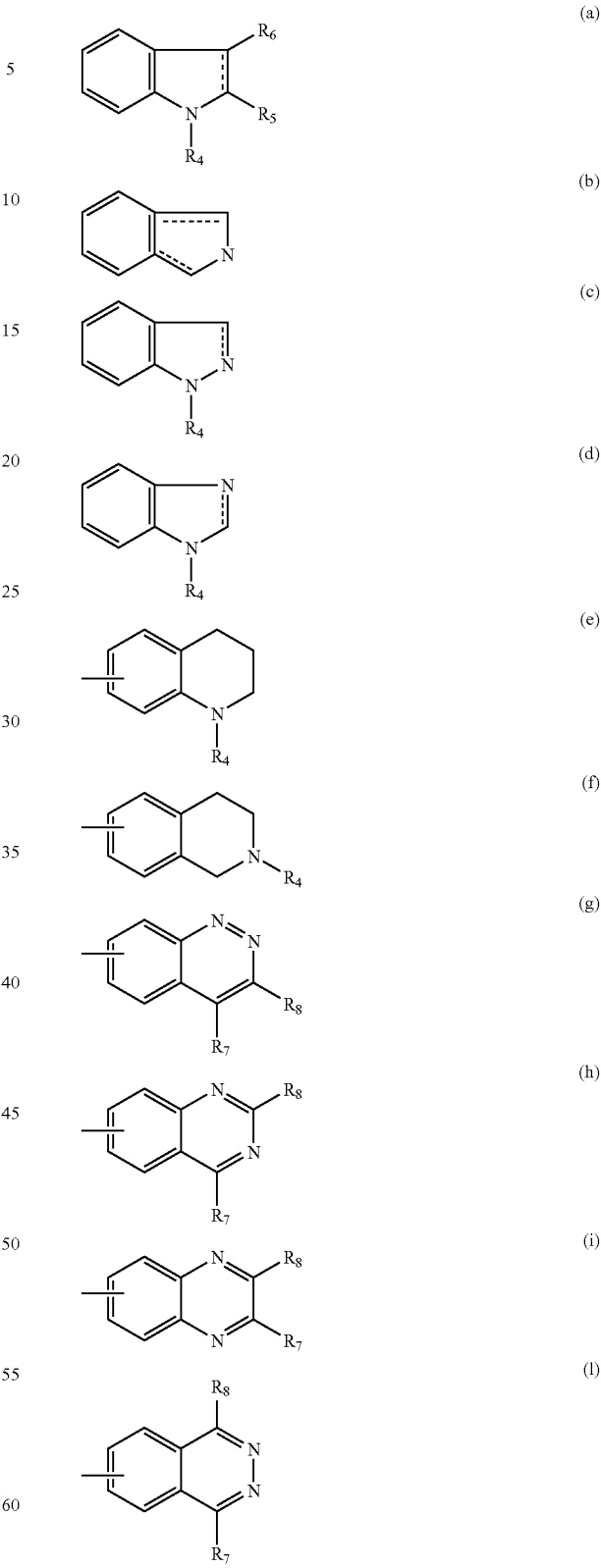

where $R_4$, $R_5$ and $R_6$ each independently represent a hydrogen atom or a $(C_1-C_4)$alkyl group;
the dotted lines represent single or double bonds;

$R_7$ and $R_8$ each independently represent a hydrogen or halogen atom or a $(C_1–C_4)$alkyl or $(C_1–C_4)$alkoxy group; and to their N-oxides and to their salts or solvates, provided that, when X is CH, then (a) is not an indol-4-yl residue.

DETAILED DESCRIPTION OF THE INVENTION

In the present description, the term "$(C_1–C_4)$alkyl" denotes a monovalent radical of a saturated, straight- or branched-chain, $C_1–C_4$ hydrocarbon and the term "$(C_1–C_4)$alkoxy" denotes a monovalent radical of a saturated, straight- or branched-chain, $C_1–C_4$ hydrocarbon bonded via an oxygen atom.

In the present description, the term "halogen" denotes an atom chosen from chlorine, bromine, iodine and fluorine.

When the dotted lines are double bonds, the heterocycles (a) to (d) represent aromatic heterocycles.

Preferred compounds of formula (I) are those where n is zero.

Other preferred compounds are those where $R_2$ and $R_3$ are each a hydrogen atom.

Other preferred compounds are those where $R_1$ is a $CF_3$ group.

Other preferred compounds are those where X is CH and $R_1$ is in the 2- or 3-position of the benzene.

Other preferred compounds are those where X is CH and $R_1$ is a $CF_3$ group.

Other preferred compounds are those where X is N and the pyridine is substituted in the 2,6-positions.

Other preferred compounds are those where $R_4$, $R_5$ and $R_6$ each represent a hydrogen or a methyl group.

Other preferred compounds are those where $R_7$ and $R_8$ each represent a hydrogen atom or a $(C_1–C_4)$alkyl group.

Other preferred compounds are those where A is a radical of formula (a)–(d), the compounds where A is a radical of formula (a) being particularly preferred.

Other preferred compounds are those where A is a radical of formula (a)–(d), in particular the radical (a), and the dotted lines represent double bonds.

The ring systems of formula (a)–(d) where the dotted lines represent double bonds can, in the present description, be named indole, isoindole, indazole and benzimidazole respectively. The rings systems of formula (a)–(d) where the dotted lines represent single bonds can, in the present description, be named indoline, isoindoline, indazoline and benzimidazoline respectively. These ring systems can be attached to the remainder of the molecule of formula (I) via any one of the carbon atoms of the 4-, 5-, 6- or 7-positions.

The ring systems of formula (e)–(f) can, in the present description, be named tetrahydroquinoline and tetrahydroisoquinoline respectively. These ring systems can be attached to the remainder of the molecule of formula (I) via any one of the carbon atoms of the 5-, 6-, 7- or 8-positions.

Other preferred compounds are those where A is a 1,4-benzodiazine of formula (i).

The ring systems of formula (g)–(i) and (l) can, in the present description, alternatively be named either 1,2-, 1,3-, 1,4- and 2,3-benzodiazines or, respectively, quinoline, quinazoline, quinoxaline and phthalazine. These benzodiazines can be attached to the remainder of the molecule of formula (I) via any one of the carbon atoms of the 5-, 6-, 7- or 8-positions.

According to the present invention, the compounds of formula (I) can exist as N-oxide derivatives. As indicated in the above formula, the compounds of formula (I) can in particular carry the N-oxide group on the tetrahyropyridine or else on one or both nitrogens of the groups (a)–(i) and (l), or else all the nitrogens present can be simultaneously oxidized.

The salts of the compounds of formula (I) according to the present invention comprise both addition salts with pharmaceutically acceptable inorganic or organic acids, such as the hydrochloride, hydrobromide, sulfate, hydrogensulfate, dihydrogenphosphate, citrate, maleate, tartrate, fumarate, gluconate, methanesulfonate, 2-naphthalenesulfonate, and the like, and addition salts which make possible suitable separation or crystallization of the compounds of formula (I), such as the picrate or oxalate, or addition salts with optically active acids, for example camphorsulfonic acids and mandelic or substituted mandelic acids.

The optically pure stereoisomers and the mixtures of isomers of the compounds of formula (I) due to the asymmetric carbon, when one of $R_2$ and $R_3$ is a methyl and the other a hydrogen, in any proportion, form part of the present invention.

The compounds of formula (I) can be prepared by a condensation reaction from a compound of formula (II):

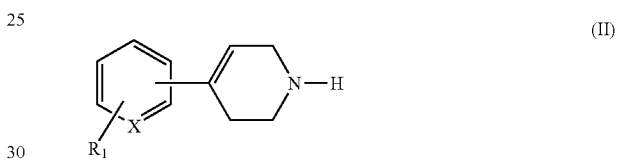

in which X and $R_1$ are as defined above, with a compound of formula (III):

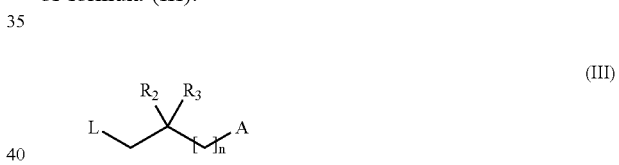

in which $R_2$, $R_3$, n and A are as defined above and L is a leaving group, isolation of the compound of formula (I) and optional conversion to one of its salts or solvates or to its N-oxide derivatives.

The condensation reaction is normally carried out by mixing the starting compounds (II) and (III) in an inert organic solvent according to conventional methods.

The term "inert organic solvent" is understood to mean a solvent which does interfere with the reaction. Such solvents are, for example, alcohols, such as methanol, ethanol, isopropanol or butanol, or ketones, such as isobutyl methyl ketone, the latter being a particularly preferred solvent.

It is possible, as leaving group L, for example, to use a chlorine or bromine atom or else a mesyloxy group ($CH_3$—$SO_2$—O—).

The reaction is carried out at a temperature of between −10° C. and the reflux temperature of the reaction mixture, the reflux temperature being preferred.

The reaction can be suitably carried out in the presence of a proton acceptor, for example of an alkaline carbonate or of a tertiary amine, such as triethylamine.

The reaction is usually brought to a conclusion after a few hours; usually from 1 to 12 hours suffice to bring the condensation to completion.

The required compound is isolated according to conventional techniques in the free base form or in the form of one of its salts. The free base can be converted to one of its salts by simple salification in an organic solvent, such as an alcohol, preferably ethanol or isopropanol, an ether, such as 1,2-dimethoxyethane, ethyl acetate, acetone or a hydrocarbon, such as hexane.

The compound of formula (I) obtained is isolated according to conventional techniques and is optionally converted to one of its salts or solvates or to its N-oxide derivatives.

The starting compounds of formula (II) are known or else they can be prepared analogously to the known compounds.

The starting compounds of formula (III) are known or else they can be prepared from the corresponding acids or esters by reduction of the carboxyl group to an alcohol group and substitution of the OH by the desired L group according to conventional methods. Examples of such reactions are recorded in the experimental part.

Alternatively, the starting compounds of formula (III) can be prepared by reaction of the organometallic derivatives of the ring systems (a)–(i) and (l) of formula (IV)

M-A    (IV)

where

M represents a metal radical and A is as defined above, with an appropriate cyclic ether, to obtain the alcohol of formula (V)

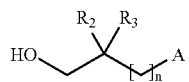    (V)

and substitution of the OH by the desired L group according to conventional methods.

The term "metal radical" is understood to mean, according to the present invention, a radical which comprises at least one metal and which is capable of opening an appropriate cyclic ether in order to give the alcohol of formula (V). Appropriate compounds of formula (IV) are, for example, Grignard compounds of formula Hal-Mg-A and cuprates Hal-Cu-A, where Hal is as defined above, lithium derivatives Li-A, and the like.

The organometallic compounds of formula (IV) are prepared according to well known techniques, for example from halogenated derivatives of the above ring systems A by reaction with magnesium or a lithium derivative; when it is desired to use a lithium derivative of the compound of formula (IV), it is appropriate to form a cuprate of said compound (IV), for example by reaction with CuI, before carrying out the opening reaction on the appropriate cyclic ether. Examples of such reactions, which are well known to a person skilled in the art, are recorded in the experimental part.

The cyclic ethers are chosen according to the compound of formula (I) which it is desired to obtain. When, for example, it is desired to prepare a compound of formula (I) where $R_2$ and $R_3$ are hydrogen and n is zero, the appropriate cyclic ether is ethylene oxide.

Alternatively, depending on the meanings of $R_2$, $R_3$ and n, ketones or aldehydes can be used instead of cyclic ethers.

The compounds of formula (I) can also be prepared by a process which plans:

(a) to react the compound of formula (VI):

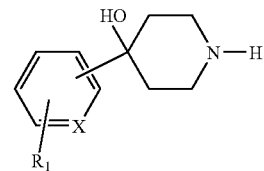    (VI)

in which X and $R_1$ are defined as above, with a functional derivative of the acid of formula (VII)

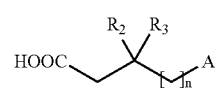    (VII)

in which $R_2$, $R_3$, n and A are as defined above, (b) to reduce the carbonyl group of the compound of formula (VIII) thus obtained:

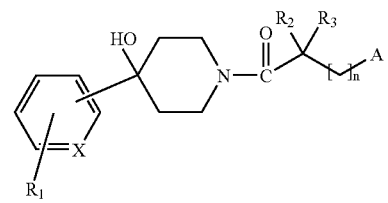    (VIII)

(c) to dehydrate the intermediate piperidinol of formula (IX) thus obtained:

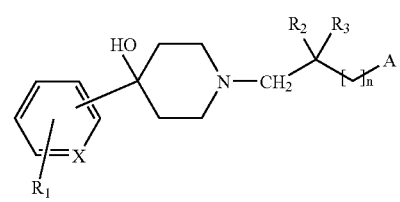    (IX)

(d) to isolate the compound of formula (I) thus obtained and, optionally, to convert it to one of its salts or solvates or to its N-oxide derivatives.

The reaction of stage (a) can be suitably carried out in an organic solvent at a temperature of between –10° C. and the reflux temperature of the reaction mixture.

It may be preferable to carry out the reaction under cold conditions when it is exothermic, as in the case where the chloride is used as functional derivative of the acid of formula (VII).

Use may be made, as appropriate functional derivative of the acid of formula (VII), of the free acid, which is optionally activated (for example with BOP=tri(dimethylamino) benzotriazol-1-yloxyphosphonium hexafluorophosphate), an anhydride, a mixed anhydride, an active ester or an acid halide, preferably the bromide. Among the active esters, the p-nitrophenyl ester is particularly preferred but the methoxyphenyl, trityl, benzhydryl and similar esters are also suitable.

Use is preferably made, as reaction solvent, of a halogenated solvent, such as methylene chloride, dichloroethane, 1,1,1-trichloroethane, chloroform and the like, but also other organic solvents compatible with the reactants employed, for example dioxane, tetrahydrofuran or a hydrocarbon, such as hexane, can likewise be employed.

The reaction can be suitably carried out in the presence of a proton acceptor, for example of an alkaline carbonate or of a tertiary amine, such as triethylamine.

The reduction of stage (b) can be suitably carried out with appropriate reducing agents, such as borane complexes, for example borane-dimethyl sulfide ($[CH_3]_2S$—$BH_3$), aluminum hydrides or a complex hydride of lithium and of aluminum, in an inert organic solvent at a temperature of between 0° C. and the reflux temperature of the reaction mixture, according to conventional techniques.

The term "inert organic solvent" is understood to mean a solvent which does not interfere with the reaction. Such solvents are, for example, ethers, such as diethyl ether, tetrahydrofuran (THF), dioxane or 1,2-dimethoxyethane.

In the reactions described above, the nitrogen atoms present on the ring systems A are preferably protected with conventional protective groups. Use may clearly be made, as protective groups, of conventional protective groups for nitrogen atoms, such as, for example, tert-butoxycarbonyl, acetyl, benzyloxycarbonyl or triisopropylsilyl, the latter being particularly preferred. These protective groups are finally cleaved off to give the compounds of formula (I).

The compounds of formula (I) carrying an N-oxide group on the nitrogen atoms of the groups (a)–(i) and (l) can be prepared from the N-oxide derivatives of the compounds of formula (VII).

The compounds of formula (I) carrying an N-oxide group on the nitrogen atom of the tetrahydro-pyridine can be prepared by oxidation of the corresponding compounds of formula (I). In this case, the compound of formula (I), such as obtained, for example, by the above synthesis, is subjected to an oxidation reaction according to conventional methods, for example to a reaction with m-chloroperbenzoic acid, in a suitable solvent, and is isolated according to conventional techniques well known to a person skilled in the art.

The compounds of the invention have properties which are advantageous with respect to the inhibition of TNF-α.

These properties were demonstrated using a test aimed at measuring the effect of molecules on TNF-α synthesis induced in Balb/c mice by lipopolysaccharide (LPS) of *Escherichia coli* (055:B5, Sigma, St Louis, Mo).

The products to be tested are administered orally to groups of 5 female Balb/c mice (Charles River, France) aged from 7 to 8 weeks. One hour later, the LPS is administered intravenously (10 μg/mouse). A blood sample is taken from each animal 1.5 hours after administration of the LPS. The samples are centrifuged and the plasma is recovered and frozen at −80° C. The TNF-α is measured using commercial kits (R and D, Abingdon, UK).

In this test, compounds representative of the invention proved to be very active, inhibiting TNF-α synthesis even at very low doses.

Due to this activity and to their low toxicity, the compounds of formula (I), including the compounds of formula (I) where X is CH and (a) is an indol-4-yl residue, and their salts or solvates can indeed be used in the treatment of diseases related to immune and inflammatory disorders or as analgesics. In particular, the compounds of formula (I) can be used to treat atherosclerosis, autoimmune diseases, diseases which lead to the demyelinization of neurones (such as multiple sclerosis), asthma, rheumatoid arthritis, fibrotic diseases, idiopathic pulmonary fibrosis, cystic fibrosis, glumerulonephritis, rheumatoid spondylitis, osteoarthritis, gout, bone and cartilage resorption, osteoporosis, Paget's disease, multiple myeloma, uveoretinitis, septic shock, septicemia, endotoxic shock, graft-versus-host reaction, graft rejection, adult respiratory distress syndrome, silicosis, asbestosis, pulmonary sarcoidosis, Crohn's disease, ulcerative colitis, amyotrophic lateral sclerosis, Alzheimer's disease, Parkinson's disease, lupus erythematosus disseminatus, hemodynamic shock, ischemic pathological conditions (myocardial infarction, myocardial ischemia, coronary vasospasm, angina pectoris, cardiac insufficiency, heart attack), postischemic reperfusion injuries, malaria, mycobacterial infections, meningitis, leprosy, viral infections (HIV, cytomegalovirus, herpes virus), AIDS-related opportunistic infections, tuberculosis, psoriasis, atopic and contact dermatosis, diabetes, cachexia, cancer and radiation-mediated damage.

The compounds of formula (I) and their pharmaceutically acceptable salts and solvates are preferably administered orally.

In the oral pharmaceutical compositions of the present invention, the active principle can be administered in unit administration forms, as a mixture with conventional pharmaceutical carriers, to animals and human beings for the treatment of the abovementioned conditions. The appropriate unit administration forms comprise, for example, tablets, optionally scored, gelatin capsules, powders, granules and solutions or suspensions to be taken orally.

When a solid composition is prepared in the form of tablets, the main active ingredient is mixed with a pharmaceutical vehicle, such as gelatin, starch, lactose, magnesium stearate, talc, gum arabic or the like. The tablets can be coated with sucrose or other appropriate materials or can be treated so that they have a prolonged or delayed activity and so that they continuously release a predetermined amount of active principle.

A preparation in the form of gelatin capsules is obtained by mixing the active ingredient with a diluent and by pouring the mixture obtained into soft or hard gelatin capsules.

A preparation in the syrup or elixir form can comprise the active ingredient in conjunction with a sweetener, preferably a calorie-free sweetener, methylparaben and propylparaben as antiseptics, and an appropriate colorant and flavoring.

The water-dispersible powders or granules can comprise the active ingredient as a mixture with dispersing agents, wetting agents or suspending agents, such as polyvinylpyrrolidone, and with sweeteners or flavor enhancers.

The active principle can also be formulated in the form of microcapsules, optionally with one or more carriers or additives.

In the pharmaceutical compositions according to the present invention, the active principle can also be in the form of an inclusion complex in cyclodextrins, their ethers or their esters.

The amount of active principle to be administered depends, as always, on the degree of progression of the disease and also on the age and weight of the patient. Nevertheless, the unit doses generally comprise from 0.001 to 100 mg, better still from 0.01 to 50 mg, preferably from 0.1 to 20 mg, of active principle, advantageously from 0.5 to 10 mg.

According to another of its aspects, the present invention relates to a combination comprising a compound of formula (I) or one of its pharmaceutically acceptable salts or solvates and at least one compound chosen from immunosuppressants, such as interferon beta-1b; adrenocorticotropic hormone; glucocorticoids, such as prednisone or methylprednisolone; or interleukin-1 inhibitors.

More particularly, the invention relates to a combination comprising a compound of formula (I) or one of its pharmaceutically acceptable salts or solvates and at least one compound chosen from roquinimex (1,2-dihydro-4-hydroxy-N,1-dimethyl-2-oxo-3-quinoline-carboxanilide), myloran (product from Autoimmune comprising bovine myelin), antegren (monoclonal human antibody from Elan/Athena Neurosciences) or recombinant interferon beta-1b.

Other possible combinations are those composed of a compound of formula (I) or one of its pharmaceutically acceptable salts or solvates and a potassium-channel blocker, such as, for example, fampridine (4-aminopyridine).

According to another of its aspects, the invention relates to a method for the treatment of diseases related to immune and inflammatory disorders and in the treatment of pain, in particular atherosclerosis, autoimmune diseases, diseases which lead to the demyelinization of neurones (such as multiple sclerosis), asthma, rheumatoid arthritis, fibrotic diseases, idiopathic pulmonary fibrosis, cystic fibrosis, glumerulonephritis, rheumatoid spondylitis, osteoarthritis, gout, bone and cartilage resorption, osteoporosis, Paget's disease, multiple myeloma, uveoretinitis, septic shock, septicemia, endotoxic shock, graft-versus-host reaction, graft rejection, adult respiratory distress syndrome, silicosis, asbestosis, pulmonary sarcoidosis, Crohn's disease, ulcerative colitis, amyotrophic lateral sclerosis, Alzheimer's disease, Parkinson's disease, lupus erythematosus disseminatus, hemodynamic shock, ischemic pathological conditions (myocardial infarction, myocardial ischemia, coronary vasospasm, angina pectoris, cardiac insufficiency, heart attack), postischemic reperfusion injuries, malaria, mycobacterial infections, meningitis, leprosy, viral infections (HIV, cytomegalovirus, herpes virus), AIDS-related opportunistic infections, tuberculosis, psoriasis, atopic and contact dermatosis, diabetes, cachexia, cancer and radiation-mediated damage, comprising the administration of a compound of formula (I), including the compounds of formula (I) where X is CH and (a) is an indol-4-yl residue, or of one of its pharmaceutically acceptable salts or solvates, alone or in combination with other active principles.

The following examples illustrate the invention.

PREPARATION METHODS

Preparation 1

2-(1-Triisopropylsilyl)-1H-indol-5-yl)ethyl Methanesulfonate 1 g of 5-bromoindole (1.0.2 mmol) is dissolved in 70 ml of anhydrous THF under a nitrogen atmosphere and at a temperature of −78° C. and the dropwise addition thereto is carried out of 15.8 ml (15.81 mmol) of LiN (SiCH$_3$)$_2$, in the form of a 1M solution in THF, and later, still at −78° C. and with care, of 3.9 ml of triisopropylsilyl chloride (TIPSiCl) (18.36 mmol). The mixture is stirred at −78° C. for 15 minutes and then at ambient temperature overnight. It is poured into a mixture composed of 100 ml of a buffer solution at pH 7 and 100 ml of brine, extraction is carried out with diethyl ether, the organic phase is washed with 1M hydrochloric acid and with water and dried over sodium sulfate, and the solvent is evaporated under reduced pressure. The product is purified by chromatography on a column of silica gel, elution being carried out with hexane. 3 g of the product thus obtained are dissolved in 30 ml of THF at −78° C. and 13.4 ml of a 1.6N solution of BuLi in hexane (21.5 mmol) are added thereto. The mixture is stirred at ambient temperature for 1 hour, is again cooled to −78° C. and is poured into a suspension of 647 mg of CuI (3.4 mmol) in a mixture of 20 g of ethylene oxide and 20 ml of THF at −78° C. The mixture is stirred at −40° C. for 5 hours and 43 ml of a solution of phosphate buffer at pH 7 are added thereto dropwise; the mixture is diluted with 17 ml of cold water and filtered through celite. The filtered solution is washed with 43 ml of 5M NH$_3$ and with cold water, the organic phase is dried over sodium sulfate and the solvent is evaporated under reduced pressure. The crude product is purified by chromatography on a column of silica gel, elution being carried out with an ethyl acetate/hexane=3/7 mixture. 1.7 g of 5-(2-hydroxy-ethyl)-1-(triisopropylsilyl)-1H-indole are thus obtained. 1 g of the alcohol thus obtained is dissolved under a nitrogen atmosphere in 15 ml of methylene chloride, and 0.44 ml of triethylamine, 384 mg of 4-dimethylaminopyridine (DMAP) and 0.243 ml of mesyl chloride are added. The mixture is stirred at ambient temperature for 2 hours and 15 ml of 3% H$_3$PO$_4$ are added thereto. The organic phase is washed with a saturated aqueous sodium bicarbonate solution, the organic phase is dried and the solvent is evaporated under reduced pressure. 1.25 g of the title product are thus obtained.

Preparation 2

2-(1-Triisopropylsilyl)-1H-indol-6-yl)ethyl Methanesulfonate

The title compound is obtained by carrying out the preparation as described in preparation 1 but by using 6-bromoindole instead of 5-bromoindole.

Preparation 3

1H-Benzimidazol-6-ylacetic Acid 1.9 g (9.04 mmol) of methyl (4-amino-3-nitrophenyl) acetate (J. Med. Chem., 1997, 40(7), 1049) are dissolved in 300 ml of methanol, and 480 mg of 10% Pd/C are added thereto. Hydrogenation is carried out at ambient temperature for 6 hours, the catalyst is filtered off and the solvent is evaporated under reduced pressure. 1.6 g of oil are thus obtained, which oil is dissolved in 18 ml of 98% formic acid and is heated at 100° C. for 5 hours. The solvent is subsequently evaporated under reduced pressure and 1.6 g of the title product are thus obtained.

Thin layer chromatography (eluent: ethyl acetate/methanol=1/1): Rf 0.35.

Preparation 4

6-(2-Chloroethyl)quinoxaline 190 mg (0.9 mmol) of ethyl (4-amino-3-nitrophenyl) acetate (obtained as described in J. Med. Chem., 1997, 40(7)) are dissolved in 30 ml of methanol, and 48 mg of 10% Pd/C are added thereto. Hydrogenation is carried out at ambient temperature for 6 hours. The catalyst is filtered off and the solvent is evaporated, producing 160 mg of oil. The product thus obtained is dissolved in 4 ml of methanol, 160 ml of 1,4-dioxane-2,3-diol are added thereto and the mixture is stirred at ambient temperature for 2 hours. The solvent is evaporated and the residue is purified by flash chromatography on a column of silica gel, elution being carried out with a cyclohexane/ethyl acetate=4/6 mixture, thus producing the ethyl ester of quinoxalin-6-ylacetic acid. The product thus obtained is dissolved in 3 ml of anhydrous diethyl ether under a stream of nitrogen. 55 mg (1.46 mmol) of LiAlH$_4$, in suspension in 2 ml of diethyl ether, are added thereto. The mixture is stirred at ambient temperature for 3.5 hours, is diluted with diethyl ether and is poured into a water/ice mixture, the phases are separated, the organic phase is dried and the solvent is evaporated. 110 mg of crude product are obtained, which product is purified by a column of silica gel, elution being carried out with ethyl acetate. 31 mg of 6-(2-hydroxy-ethyl)quinoxaline are thus obtained, which product is dissolved in 0.5 ml of anhydrous methylene chloride under a stream of nitrogen. The solution is cooled to 0° C., 0.3 ml of SOCl$_2$ is added thereto dropwise and the mixture is stirred at 0° C. for two hours and then at ambient temperature overnight. Methylene chloride and water are added, the solution is brought to basic pH by addition of NaHCO$_3$, extraction is carried out with methylene chloride and the two phases are separated. The organic phase is dried and the solvent is evaporated. 34 mg of the title product are thus obtained.

Preparation 5

6-(2-Chloroethyl)-2,3-dimethylquinoxaline

The title compound is obtained by carrying out the preparation as described in preparation 4 but by using 1,3-butanedione instead of 1,4-dioxane-2,3-diol.

Preparation 6

6-(2-bromoethyl)-2,3-diethylquinoxaline

The title compound is obtained by carrying out the preparation as described in preparation 4 but by using 3,4-hexanedione instead of 1,4-dioxane-2,3-diol and by treating the intermediate alcohol 6-(2-hydroxyethyl)-2,3-diethylquinoxaline thus obtained with hydrobromic acid instead of SOCl$_2$.

EXAMPLES

EXAMPLE 1

5-[2-(4-(3-(Trifluoromethyl)phenyl)-1,2,3,6-tetrahydro-pyrid-1-yl)ethyl]-1H-indole A mixture of 1 g (3.78 mmol) of 4-hydroxy-4-(3-(trifluoromethyl)phenyl)-1,2,3,6-tetrahydropyridine and 1.2 ml of triethylamine (8.71 mmol) in 10 ml of isopropanol is stirred at ambient temperature for 10 minutes. 1.2 g of 2-((1-triisopropylsilyl)-1H-indol-5-yl)ethyl methanesulfonate from preparation 1, dissolved in 10 ml of isopropanol, are added thereto and the mixture is heated at reflux for 12 hours. The solvent is subsequently evaporated under reduced pressure and the crude product is purified by chromatography on a column of silica gel, elution being carried out with a hexane/ethyl acetate=7/3 mixture. The condensation product is thus obtained. 0.9 g of the product thus obtained is dissolved in 15 ml of THF and the solution is cooled to 0° C. 0.66 g of tetrabutylammonium fluoride (Bu$_4$NF.3H$_2$O) (2.1 mmol) is added thereto. The mixture is stirred at ambient temperature for 1 hour, the solvent is subsequently evaporated and the crude product is purified by chromatography on a column of silica gel, elution being carried out with a hexane/ethyl acetate=4/6 mixture. The product obtained is washed in hexane and filtered off, and 0.4 g of the title product is thus obtained.

M.p. 122–123° C.

EXAMPLE 2

6-[2-(4-(3-(Trifluoromethyl)phenyl)-1,2,3,6-tetrahydro-pyrid-1-yl)ethyl]-1H-indole The title compound is obtained by carrying out the preparation as described in example 1 but by using the product from preparation 2 instead of the product from preparation 1.

M.p. 168–169° C.

Thin layer chromatography (eluent: cyclohexane/ethyl acetate=1/1): Rf 0.2.

EXAMPLE 3

6-[2-(4-(3-(Trifluoromethyl)phenyl)-1,2,3,6-tetrahydro-pyrid-1-yl)ethyl]-1H-benzimidazole and its Dihydrochloride 3a) 1-[4-Hydroxy-4-(3-(trifluoromethyl)phenyl)-1-piperidinyl]-2-(6-benzimidazolyl)-1-ethanone A mixture of 1.46 g (0.0083 mol) of 1H-benzimidazol-6-ylacetic acid from preparation 3, 2.0 g (0.0081 mol) of 4-hydroxy-4-(3-(trifluoromethyl)phenyl)piperidine, 3.6 g of BOP and 3.4 ml of triethylamine in 40 ml of dimethylformamide is stirred at ambient temperature overnight. A mixture of ethyl acetate and of water is added, the two phases are separated, the organic phase is dried over sodium sulfate and the solvent is evaporated. The crude product is purified by chromatography on a column of silica gel, elution being carried out with an ethyl acetate/methanol=9/1 mixture, and the title compound is thus obtained.

3b) 6-[2-(4-Hydroxy-4-(3-(trifluoromethyl)phenyl)-piperidin-1-yl)ethyl]-1H-benzimidazole 1 g of the product obtained with example 3a is dissolved in 18 ml of anhydrous THF under a stream of nitrogen, the mixture is heated at reflux for 30 minutes, 1 ml of borane-dimethyl sulfide in 13.5 ml of THF is added thereto and the mixture is heated at reflux for 4 hours. The mixture is cooled, 13.5 ml of ethanol are added thereto and the mixture is heated at reflux for 30 minutes. The solvent is evaporated, the residue is taken up in an ethyl acetate/dilute NH$_4$OH mixture, the two phases are separated and the organic phase is washed with water. The organic phase is dried over sodium sulfate and the solvent is evaporated under reduced pressure. The crude product is purified by chromatography on a column of silica gel, elution being carried out with an ethyl acetate/methanol=8/2 mixture. 0.540 g of the title product is obtained in the form of an oil.

3c) 6-[2-(4-(3-(Trifluoromethyl)phenyl)-1,2,3,6-tetrahydro-pyrid-1-yl)ethyl]-1H-benzimidazole and its Dihydrochloride 0.540 g of the product from the preceding stage is dissolved in 6.5 ml of acetic acid, 1.5 ml of 96% sulfuric acid are added thereto and the mixture is heated at 80° C. for 1 hour. The mixture is poured into an NaOH/ice mixture and extraction is carried out with ethyl acetate. The organic phase is washed with water, dried and evaporated under reduced pressure. The title compound is thus obtained. The dihydrochloride salt is prepared using a solution of isopropanol saturated with hydrochloric acid.

M.p. (dihydrochloride) 260–263° C.

EXAMPLE 4

7-[2-(4-(3-(Trifluoromethyl)phenyl)-1,2,3,6-tetrahydro-pyrid-1-yl)ethyl]-N-methyl-1,2,3,4-tetrahydroiso-quinoline and its dihydrochloride Hydrate The title compound is obtained by carrying out the preparation as described in example 3 but by using N-methyl-1,2,3,4-tetrahydroisoquinol-7-ylacetic acid instead of 1H-benzimidazol-6-ylacetic acid.

M.p. (dihydrochloride hydrate) 180° C.

EXAMPLE 5

7-[2-(4-(3-(Trifluoromethyl)phenyl)-1,2,3,6-tetrahydro-pyrid-1-yl)ethyl]-1,2,3,4-tetrahydroisoquinoline 100 mg of the product from example 4 (base, 30 mmol) are dissolved in 1.5 ml of 1-chloroethyl chloroformate and the mixture is heated at 80° C. for 6 hours. 5 ml of methanol are added and the mixture is heated at reflux for 1 hour. The solvent is evaporated under reduced pressure and the crude product is purified by chromatography on a column of silica gel, elution being carried out with methanol. The title product is thus obtained.

Thin layer chromatography: (eluent: 100% methanol): Rf 0.4.

EXAMPLE 6

6-[2-(4-(3-(Trifluoromethyl)phenyl)-1,2,3,6-tetrahydro-pyrid-1-yl)ethyl]-4-methoxyquinazoline The title compound is obtained by carrying out the preparation as described in example 3 but by using 4-methoxyquinazol-6-ylacetic acid instead of 1H-benzimidazol-6-ylacetic acid.

EXAMPLE 7

6-[2-[4-(3-(Trifluoromethyl)phenyl)-1,2,3,6-tetrahydropyrid-1-yl]ethyl]quinoxaline and its dihydrochloride 340 mg (1.78 mmol) of 6-(2-chloroethyl)-quinoxaline from preparation 4 are dissolved in 12 ml of isopropanol, and 791 mg (3.56 mmol) of 4-(3-(trifluoromethyl)phenyl)-1,2,3,6-tetrahydropyridine are added thereto. The mixture is heated at reflux for 4 hours and is then stirred at ambient temperature overnight. The solvent is evaporated under reduced pressure and the crude product is obtained, which product is purified by chromatography on a column of silica gel, elution being carried out with ethyl acetate. The title product is thus obtained. Its dihydrochloride salt is prepared by reaction with hydrochloric acid in isopropanol.

M.p. (dihydrochloride) 239–241° C.

EXAMPLE 8

6-[2-[4-(3-(Trifluoromethyl)phenyl)-1,2,3,6-tetrahydropyrid-1-yl]ethyl]-2,3-dimethylquinoxaline and its Dihydrochloride The title compound is obtained by carrying out the preparation as described in example 7 but by using 6-(2-chloroethyl)-2,3-dimethylquinoxaline from preparation 5.

M.p. (dihydrochloride) 209–212° C.

EXAMPLE 9

6-[2-[4-(3-(Trifluoromethyl)phenyl)-1,2,3,6-tetrahydropyrid-1-yl]ethyl]-2,3-diethylquinoxaline and its Dihydrochloride The title compound is obtained by carrying out the preparation as described in example 7 but by using 6-(2-bromoethyl)-2,3-diethylquinoxaline from preparation 6.

M.p. (dihydrochloride) 210–212° C.

EXAMPLE 10

6-[2-[4-(6-(Trifluoromethyl)pyrid-2-yl)-1,2,3,6-tetrahydropyrid-1-yl]ethyl]quinoxaline and its Oxalate The title compound is obtained by carrying out the preparation as described in example 7 but by using 4-(6-(trifluoromethyl)pyrid-2-yl)-1,2,3,6-tetra-hydropyridine instead of 4-(3-(trifluoromethyl)phenyl)-1,2,3,6-tetrahydropyridine.

M.p. (oxalate) 125–128° C.

EXAMPLE 11

6-[2-[4-(3-(Trifluoromethyl)phenyl)-1,2,3,6-tetrahydro-pyrid-1-yl]ethyl]phthalazine The title compound is obtained by carrying out the preparation as described in example 3 but by using phthalaz-6-ylacetic acid.

Thin layer chromatography (eluent: ethyl acetate/methanol=8/2): Rf 0.4.

What is claimed is:

1. A compound of formula (I):

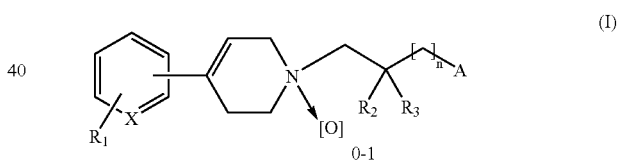

in which
X represents N or CH;
$R_1$ represents a hydrogen or halogen atom or a $CF_3$ group;
$R_2$ and $R_3$ independently represent a hydrogen atom or a methyl group;
n is 0 or 1;
A represents a nitrogenous heterocycle of formula (a)–(i) and: (l):

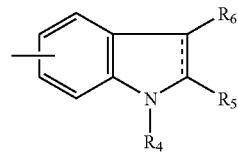

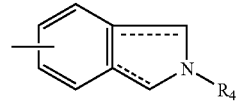

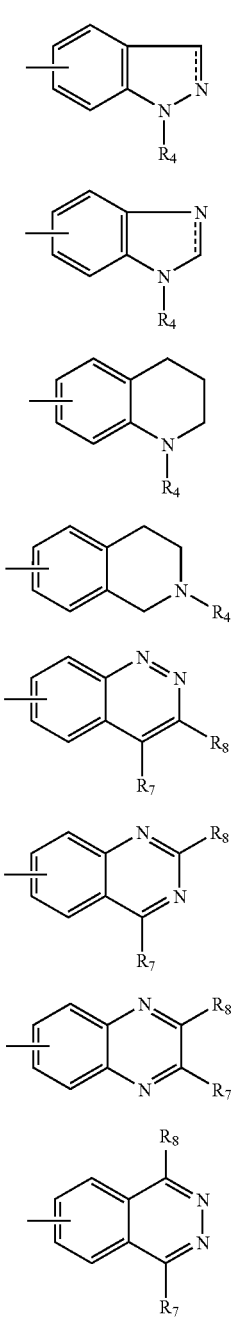

where $R_4$, $R_5$ and $R_6$ each independently represent a hydrogen atom or a $(C_1-C_4)$alkyl group;

the dotted line with a solid line represent single or double bond;

$R_7$ and $R_8$ each independently represent a hydrogen or halogen atom or a $(C_1-C_4)$alkyl or $(C_1-C_4)$alkoxy group; or an N-oxide, salt or solvates, thereof;

provided that, when X is CH, then A is not an indol-4-yl moiety of formula (a).

2. The compound according to claim 1, where n is zero.

3. The compound according to claim 1, where $R_2$ and $R_3$ are each a hydrogen.

4. The compound according to claim 1, where $R_1$ is a $CF_3$ group.

5. The compound as claimed in claim 1, where X is CH and $R_1$ is in the 3-position of the benzene.

6. The compound according to claim 1, where X is CH and $R_1$ is in the 2-position of the benzene.

7. The compound according to claim 1, where X is N and the pyridine is substituted in the 2,6-positions.

8. The compound according to claim 1, where $R_4$, $R_5$ and $R_6$ each independently represent a hydrogen atom or a $(C_1-C_4)$alkyl group.

9. The compound according to claim 1, where A is the nitrogenous heterocycle of formula (a).

10. The compound according to claim 1, where $R_7$ and $R_8$ each independently represent a hydrogen atom or a $(C_1-C_4)$ alkyl group.

11. The compound according to claim 1, where A is is the nitrogenous heterocycle of formula (i).

12. The compound according to any one of claims 1 to 11, in the form of its N-oxide derivatives.

13. The compound according to claim 1, chosen from,
5-[2-(4-(3-(Trifluoromethyl)phenyl)-1,2,3,6-tetrahydro-pyrid-1-yl)ethyl]-1H-indole;
6-[2-(4-(3-(Trifluoromethyl)phenyl)-1,2,3,6-tetrahydro-pyrid-1-yl)ethyl]-1H-indole;
6-[2-(4-(3-(Trifluoromethyl)phenyl)-1,2,3,6-tetrahydro-pyrid-1-yl)ethyl]-1H-benzimidazole;
7-[2-(4-(3-(Trifluoromethyl)phenyl)-1,2,3,6-tetrahydro-pyrid-1-yl)ethyl]-N-methyl-1,2,3,4-tetrahydroiso-quinoline;
7-[2-(4-(3-(Trifluoromethyl)phenyl)-1,2,3,6-tetrahydro-pyrid-1-yl)ethyl]-1,2,3,4-tetrahydroisoquinoline;
6-[2-(4-(3-(Trifluoromethyl)phenyl)-1,2,3,6-tetrahydro-pyrid-1-yl)ethyl]-4-methoxyquinazoline;
6-[2-[4-(3-(Trifluoromethyl)phenyl)-1,2,3,6-tetrahydro-pyrid-1-yl]ethyl]quinoxaline;
6-[2-[4-(3-(Trifluoromethyl)phenyl)-1,2,3,6-tetrahydro-pyrid-1-yl]ethyl]-2,3-dimethylquinoxaline;
6-[2-[4-(3-(Trifluoromethyl)phenyl)-1,2,3,6-tetrahydro-pyrid-1-yl]ethyl]-2,3-diethylquinoxaline;
6-[2-[4-(6-(Trifluoromethyl)pyrid-2-yl)-1,2,3,6-tetrahy-dro-pyrid-1-yl]ethyl]quinoxaline; and
6-[2-[4-(3-(Trifluoromethyl)phenyl)-1,2,3,6-tetrahydro-pyrid-1-yl]ethyl]phthalazine; or
the N-oxide, salt or solvate thereof.

14. A process for the preparation of a compound of formula (I) according to claim 1, which comprises the reaction of a compound of formula (II)

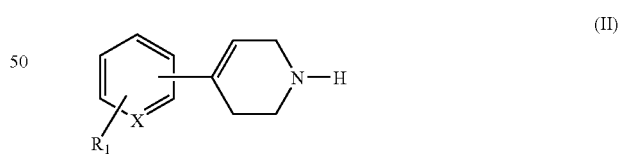

with a compound of formula (III):

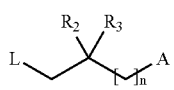

in which $R_1$, X, $R_2$, $R_3$, n and A are as defined in claim 1 and L is a leaving group, isolation of the compound of formula (I) and optional conversion to one of its salts or solvates or to its N-oxide derivatives.

15. A pharmaceutical composition, comprising, as active principle, a compound according to claim 1 together with a pharmaceutically acceptable carrier.

16. The composition according to claim 15, which comprises from 0.001 to 100 mg of active principle.

17. A pharmaceutical composition, comprising, as active principle, a compound according to claim 13 together with a pharmaceutically acceptable carrier.

18. A method of producing analgesia in a patient in need thereof which comprises administering to said patient an analgesically effective amount of a compound according to claim 13.

19. A method for the treatment of a disease related to pain, osteoarthritis or rheumatoid arthritis which comprises administering to a patient in need of such treatment an effective amount of a compound of formula (I)

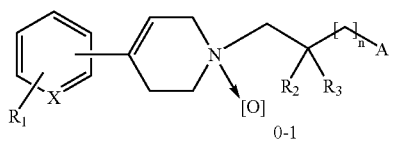

(I)

in which

X represents N or CH;

$R_1$ represents a hydrogen or halogen atom or a $CF_3$ group;

$R_2$ and $R_3$ independently represent a hydrogen atom or a methyl group;

n is 0 or 1;

A represents a nitrogenous heterocycle of formula (a)–(i) and (l):

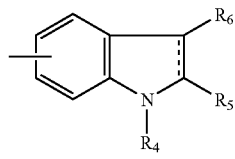
(a)

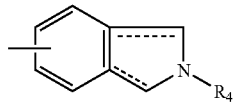
(b)

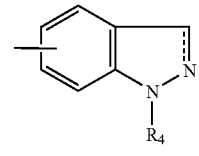
(c)

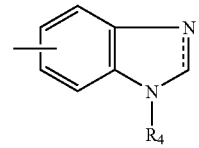
(d)

-continued

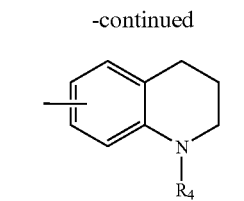
(e)

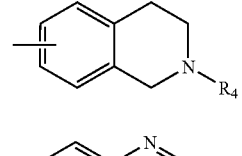
(f)

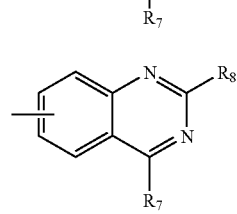
(g)

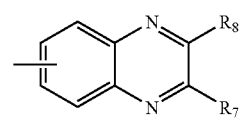
(h)

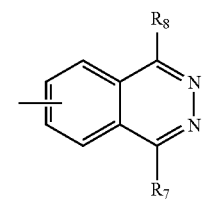
(i)

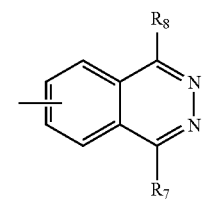
(l)

where $R_4$, $R_5$ and $R_6$ each independently represent a hydrogen atom or a ($C_1$–$C_4$)alkyl group;

the dotted line with a solid line represent a single or double bond;

$R_7$ and $R_8$ each independently represent a hydrogen or halogen atom or a ($C_1$–$C_4$)alkyl or ($C_1$–$C_4$)alkyl group;

or an N-oxide or pharmaceutically acceptable salt or solvate thereof; provided that, when X is CH, then A is not an indol-4-yl moiety of formula (a).

20. A method for the treatment of a disease related to pain, osteoarthritis or rheumatoid arthritis which comprises administering to a patient in need of such treatment an effective amount of a compound according to claim 13.

* * * * *